(12) United States Patent
Cavallazzi et al.

(10) Patent No.: US 10,729,420 B2
(45) Date of Patent: Aug. 4, 2020

(54) TWO-PIECE SUTURE ANCHOR AND SYSTEM

(71) Applicant: Biomet Sports Medicine, LLC, Warsaw, IN (US)

(72) Inventors: Cesare Cavallazzi, Miami, FL (US); Robert F. Graham, Miami, FL (US); Driany Alfonso, Surfside, FL (US)

(73) Assignee: Biomet Sports Medicine, LLC, Warsaw, IN (US)

( * ) Notice: Subject to any disclaimer, the term of this patent is extended or adjusted under 35 U.S.C. 154(b) by 391 days.

(21) Appl. No.: 15/133,969

(22) Filed: Apr. 20, 2016

(65) Prior Publication Data

US 2016/0310127 A1 Oct. 27, 2016

Related U.S. Application Data

(60) Provisional application No. 62/152,285, filed on Apr. 24, 2015.

(51) Int. Cl.
*A61B 17/04* (2006.01)

(52) U.S. Cl.
CPC .. *A61B 17/0401* (2013.01); *A61B 2017/0403* (2013.01); *A61B 2017/0409* (2013.01); *A61B 2017/0445* (2013.01); *A61B 2017/0451* (2013.01); *A61B 2017/0458* (2013.01)

(58) Field of Classification Search
CPC ........ A61B 17/0401; A61B 2017/0403; A61B 2017/0409; A61B 2017/0445; A61B 2017/0451; A61B 2017/0458; A61B 2017/0456; A61B 2017/044; A61B 2017/045

See application file for complete search history.

(56) References Cited

U.S. PATENT DOCUMENTS

| 5,725,529 | A | * | 3/1998 | Nicholson | A61B 17/0401 606/232 |
| 2008/0275469 | A1 | * | 11/2008 | Fanton | A61B 17/0401 606/139 |
| 2010/0292732 | A1 | * | 11/2010 | Hirotsuka | A61B 17/0401 606/232 |
| 2014/0081325 | A1 | * | 3/2014 | Sengun | A61B 17/0401 606/232 |

* cited by examiner

*Primary Examiner* — Kathleen S Holwerda
*Assistant Examiner* — Brooke Labranche
(74) *Attorney, Agent, or Firm* — Schwegman Lundberg & Woessner, P.A.

(57) ABSTRACT

Systems and apparatuses for soft tissue repair including a device for anchoring sutured tissue to a bone are disclosed. According to one example, the device can include an outer body and an inner member. The outer body can comprise a shell with an outer surface configured to engage the bone of a patient and an inner passage extending longitudinally from a proximal end portion toward a distal end portion. The inner member can be configured to be disposed within the outer body and can be moveable along the inner passage relative to the outer body between a first position and a second position. The inner member can be configured with an eyelet to receive and pass a suture through the member and at least one of the outer body and the inner member can have a first groove extending generally longitudinally along at least a portion thereof. The first groove can be configured to receive the suture therein.

13 Claims, 9 Drawing Sheets

TWO-PIECE SUTURE ANCHOR AND SYSTEM

CLAIM OF PRIORITY

This application claims the benefit of U.S. Provisional Patent Application Ser. No. 62/152,285, filed on Apr. 24, 2015, the benefit of priority of which is claimed hereby, and which is incorporated by reference herein in its entirety.

FIELD

The present subject matter relates to surgical procedures and devices and, more particularly, to prostheses and systems related to soft tissue repair.

BACKGROUND

The successful reattachment of soft tissue to bone can be a significant concern, especially in the sports medicine industry.

The majority of soft tissue repairs involve suture anchors or tacks. In such methods, an anchor or tack is readied for insertion into bone and a suture is passed through tissue and the anchor or tack and knotted or otherwise connected thereto. While holding tension on the suture, joint stability is evaluated and the anchor or tack is deployed into the bone, finalizing the repair.

OVERVIEW

This disclosure pertains generally to systems and devices that facilitate the rapid connection of sutures to tissue fixation implants such as a suture anchor. For example, the systems and devices can facilitate the passage of one or more sutures through the suture anchor and the connection of the one or more sutures to the suture anchor. Such connection between the suture anchor and the suture can be accomplished with a minimal change in tension on the one or more sutures from prior to and after deployment of the suture anchor into bone. Deployment of the suture anchor into bone can be accomplished by a deployment tool, which provides the ability to rapidly and precisely deliver the suture anchor to a desired location, affix the suture anchor to bone and secure the suture to the suture anchor as will be described herein.

The present inventor has recognized, among other things, that existing soft tissue fixation solutions can require a multiple step process where connection of the suture to the suture anchor can be challenging and time consuming. This process can include deploying an anchor into bone and connecting suture(s) to the deployed anchor. It can often be difficult to accomplish such connection as the suture(s) must be knotted or otherwise connected while maintaining the suture at a desired amount of tension. Failure to provide adequate tension (providing too much or too little) can cause the suture(s) to be ineffective necessitating repetition of the entire process in some cases.

Considering these and other factors, the present inventor proposes an anchoring device and related systems and techniques that can reduce the number of currently used surgical processes to provide for faster, easier, and more reproducible surgical techniques. Thus, the present application discloses an anchor device configuration where upon deployment of the anchor device, connection of the suture(s) to the anchor is accomplished and a desired tension is substantially maintained during this process.

To further illustrate the apparatuses and systems disclosed herein, the following non-limiting examples are provided:

Example 1 is a device for anchoring sutured tissue to a bone, the device can comprise: an outer body comprising a shell with an outer surface thereof configured to engage the bone of a patient and an inner passage extending longitudinally from a proximal end portion thereof toward a distal end portion; and an inner member configured to be disposed within the body and moveable along the inner passage relative to the body between a first position and a second position, wherein the inner member is configured with an eyelet to receive and pass a suture through the inner member, at least one of the outer body and the inner member having a first groove extending generally longitudinally along at least a portion thereof, the first groove configured to receive the suture therein.

In Example 2, the subject matter of Example 1 optionally includes wherein an inner surface that defines the inner passage of the outer body has a tapered section along the proximal end portion, and wherein a proximal end portion of the inner member has an exterior surface defining a tapered section, the tapered section of the inner member is configured to engage with the tapered section of the outer body and create an interference fit where the inner member is compressed against the outer body when the inner member is in the second position.

In Example 3, the subject matter of Example 2 optionally includes wherein the inner surface of the outer body has a non-tapered section distal of the tapered section thereof and the exterior surface of the inner member has a non-tapered section distal of the tapered section thereof, and wherein the non-tapered section of the inner member is configured to engage with the non-tapered section of the outer body and create an interference fit where the inner member is compressed against the outer body when the inner member is in the second position.

In Example 4, the subject matter of Example 3 optionally includes wherein the outer body has one or more features on an inner surface that defines the inner passage configured to mate with corresponding one or more features on the exterior surface of the inner member.

In Example 5, the subject matter of Example 4 optionally includes wherein the one or more features comprise one or more of grooves and threads.

In Example 6, the subject matter of any one or more of Examples 1-5 optionally include wherein the inner member has at least a first portion, a second portion, and a third portion along at least a part of a circumference of an external surface thereof, and wherein the first portion, the second portion, and the third portion each have a differently configured periphery with respect to one another.

In Example 7, the subject matter of Example 6 optionally includes wherein the first portion comprises a periphery corresponding to that of the first groove in the cross-section, the second portion comprises a periphery corresponding to that of a second groove in the cross-section, and the third portion comprises a periphery corresponding to that of a mating feature.

In Example 8, the subject matter of any one or more of Examples 1-7 optionally include a second groove extending generally longitudinally along at least a portion of an exterior surface of the inner member.

In Example 9, the subject matter of Example 8 optionally includes wherein the second groove is disposed on an opposing circumferential side of the exterior surface of the inner member from the first groove, and wherein the first groove and the second groove each extend from a proximal end of the inner member to communicate with the eyelet.

In Example 10, the subject matter of any one or more of Examples 1-9 optionally include wherein the inner member has a coupling feature disposed at a proximal end portion thereof, the coupling feature configured to mate with an actuation member that advances the inner member from the first position to the second position.

In Example 11, the subject matter of any one or more of Examples 1-10 optionally include wherein the inner member is configured as a compression plug that is configured to engage and be compressed against an inner surface that defines the inner passage of the outer body when the inner member is in the second position, and wherein only a first portion of a periphery of the inner member is configured to engage and be compressed against the inner surface and a second portion of the periphery of the inner member comprises the first groove and a second groove configured to receive the suture therein.

Example 12 is a system for anchoring a sutured tissue to a bone, the system can comprise: a suture; an outer body comprising a shell with an outer surface thereof configured to engage the bone of a patient and an inner passage extending longitudinally from a proximal end portion thereof toward a distal end portion; an inner plug configured to be disposed within the outer body and moveable along the inner passage relative to the outer body between a first position and a second position, wherein the inner plug is configured to engage and be compressed against an inner surface that defines the inner passage of the outer body when the inner plug is in the second position, the inner plug having an eyelet configured to receive and pass the suture through the inner plug; and a surgical tool configured to actuate movement of the inner plug relative to the outer body between the first position and the second position via a deployment member that is coupleable to the inner plug, the deployment member configured to be detachable from the inner plug.

In Example 13, the subject matter of Example 12 optionally includes wherein the surgical tool has an outer cannula, an inner shaft residing inside and movable relative to the outer cannula, and the deployment member is coupled to and extends from a distal end of the inner shaft, and wherein the inner shaft is coupled to an actuation device that is configured to be depressed by the user to facilitate a movement of the actuation device, the inner shaft and the deployment member.

In Example 14, the subject matter of Example 13 optionally includes wherein the actuation device is at least partially disposed within an outer housing comprising a handle, and wherein a portion of the outer housing is configured to be removable from a second portion of the outer housing thereby allowing the actuation device to be depressed by the user.

In Example 15, the subject matter of any one or more of Examples 12-14 optionally include a threading tool, the threading tool having a loop configured to receive the one or more sutures and fit through the eyelet, and wherein the threading tool is configured to be mountable to the surgical tool.

In Example 16, the subject matter of any one or more of Examples 12-15 optionally include wherein only a first portion of a periphery of the inner plug is configured to engage and be compressed against the inner surface and a second portion of the periphery of the inner plug comprises one or more grooves configured to receive the suture therealong, wherein the suture is captured between the inner plug and the outer body when the inner plug is in the second position.

In Example 17, the subject matter of any one or more of Examples 12-16 optionally include wherein the inner surface of the outer body has a tapered section along the proximal end portion and a proximal end portion of the inner plug has a tapered section, the tapered section of the inner plug is configured to engage with and be compressed against the tapered section of the outer body when the inner plug is in the second position.

Example 18 is a two-piece suture anchor for anchoring sutured tissue to a bone, the suture anchor can comprise: an outer body comprising a shell with an outer surface thereof configured to engage the bone of a patient and an inner passage extending longitudinally from a proximal end portion thereof toward a distal end portion; and an inner plug configured to be disposed within the outer body and moveable along the inner passage relative to the outer body between a first position and a second position, wherein the inner plug is configured to engage and be compressed against an inner surface that defines the inner passage of the outer body when the inner plug is in the second position, the inner plug having an eyelet and one or more grooves configured to receive and pass a suture along at least a portion of the inner plug and through the inner plug.

In Example 19, the subject matter of Example 18 optionally includes wherein only a first portion of a periphery of the inner plug is configured to engage and be compressed against the inner surface and a second portion of the periphery of the inner plug comprises the one or more grooves configured to receive the suture therein, the suture captured between the inner plug and the outer body when the inner plug is in the second position.

In Example 20, the subject matter of any one or more of Examples 18-19 optionally include wherein the inner surface of the outer body has a tapered section along the proximal end portion and a proximal end portion of the inner plug has a tapered section, the tapered section of the inner plug is configured to engage with and be compressed against the tapered section of the outer body when the inner plug is in the second position.

These and other examples and features of the present apparatuses, and systems will be set forth in part in the following Detailed Description. This Overview is intended to provide non-limiting examples of the present subject matter—it is not intended to provide an exclusive or exhaustive explanation. The Detailed Description below is included to provide further information about the present apparatuses, systems and methods.

BRIEF DESCRIPTION OF THE DRAWINGS

In the drawings, which are not necessarily drawn to scale, like numerals can describe similar components in different views. Like numerals having different letter suffixes can represent different instances of similar components. The drawings illustrate generally, by way of example, but not by way of limitation, various examples discussed in the present document.

DETAILED DESCRIPTION

The present application relates to systems and devices that facilitate the connection of sutures to tissue fixation implants such as a suture anchor. For example, the systems and devices can facilitate the passage of one or more sutures through the suture anchor and the connection of the one or more sutures to the suture anchor with a minimal change in tension on the one or more sutures from prior to and after deployment of the suture anchor into bone. The present tissue fixation implants have applicability to a variety of orthopedic procedures as well as to the sports medicine industry. Thus, the present implants are applicable to the repair of and/or fixation to various anatomical locations and features including, for example, the labrum of the shoulders.

Figures 1, 1A:
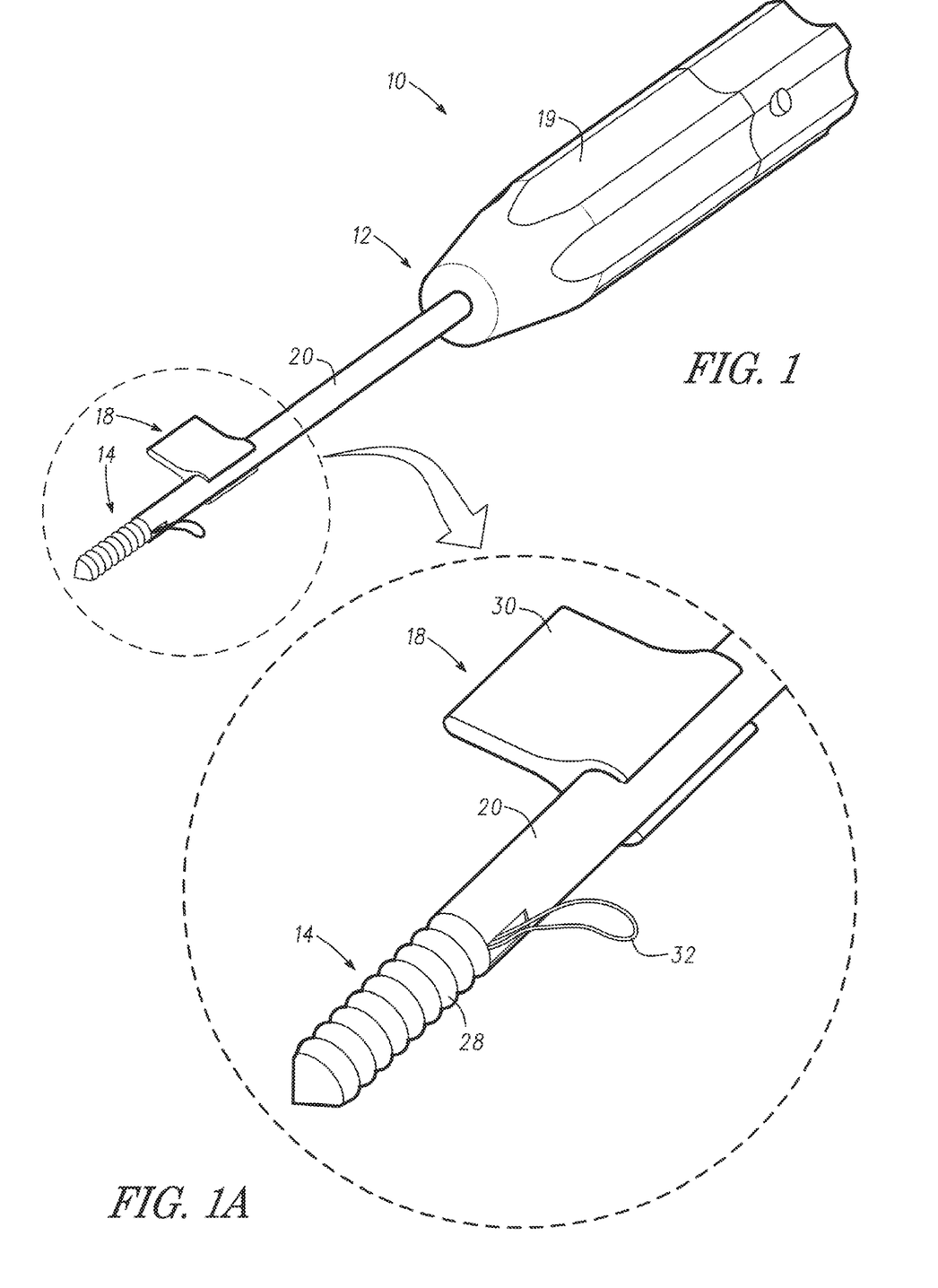
FIG. 1 illustrates a system for soft tissue repair including an anchoring device and a deployment tool in accordance with an example of the present application.
FIG. 1A shows an enlargement of a distal portion of the system of FIG. 1 further illustrating a loop of a threading device passed through the anchoring device of the system in accordance with an example of the present application.

FIG. 1 shows a system 10 for repair of soft tissue. The system 10 includes a deployment tool 12, an implantable anchor 14, one or more sutures 16 (FIGS. 7 and 8), and a threading device 18.

The deployment tool 12 can be configured for facilitating fixation of the implantable anchor 14 into bone of a patient. As such, the deployment tool 12 can have a proximal handle 19 that can be contacted (e.g., tapped) by a tool such as a mallet to initially place and secure the implantable anchor 14 into a cavity in bone. As is shown in FIG. 1 and the enlargement of the distal portion of the deployment tool 12 in FIG. 1A, the deployment tool 12 can have an outer cannula 20, an inner shaft 23 (FIGS. 2 and 9) residing inside and movable relative to the outer cannula 20, and a deployment member 22 (FIGS. 2 and 7) coupled to and extending from a distal end of the inner shaft 23.

Further discussion of the construction and relative movement of various of the components of the system 10 will be described in further detail with regard to FIGS. 9 and 10.

Figure 2:
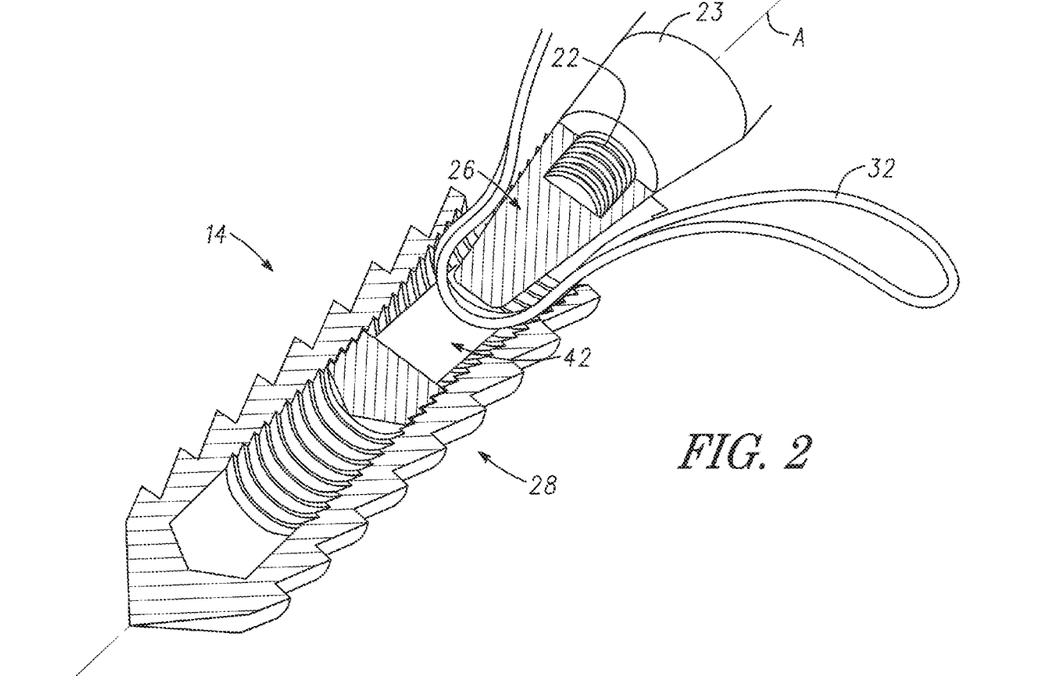
FIG. 2 shows a cross-sectional view of the anchoring device with an inner member in a non-deployed position and with the loop of the threading device passing through the inner member in accordance with an example of the present application.

The deployment tool 12 can be configured to couple with the implantable anchor 14 (via deployment member 22 of FIG. 2) and can actuate one portion (an inner member 26 as shown in FIG. 2) of the implantable anchor 14 relative to another portion (an outer body 28) in a manner to be discussed subsequently. FIG. 2 provides an example of the inner member 26 and the outer body 28 in a non-deployed first position. As used herein, the inner member 26 can be referred to as a plug or a compression plug herein.

As shown in FIG. 1A the threading device 18 can include a body portion 30 configured to couple to the outer cannula 20 or another portion of the deployment tool 12. The threading device 18 can additionally include a loop 32 constructed of a flexible material such as fiber. The loop 32 can couple to the body portion 30. The loop 32 can be configured for insertion into the outer body 28 of the implantable anchor 14 and through the inner member 26 (FIG. 2) in a manner that will be discussed and illustrated subsequently. The loop 32 can be configured to receive the one or more sutures 16 (FIGS. 7 and 8) and can fit through grooves or other passages between the inner member 26 (FIG. 2) and the outer body 28. The loop 32 can further be configured to pass through an eyelet of the inner member 26 (FIG. 2) as will be discussed and illustrated subsequently. The loop 32 can act to draw the suture(s) 16 into and out of the outer body 28 and through the inner member 26 (FIG. 2) prior to deployment of the implantable anchor 14 into bone. Once the suture(s) 16 has been drawn into and out of the outer body 28 and through the inner member 26 (FIG. 2), the loop 32 can be withdrawn from the implantable anchor 14 and the threading tool 18 can be removed from the deployment tool 12.

Figure 3:
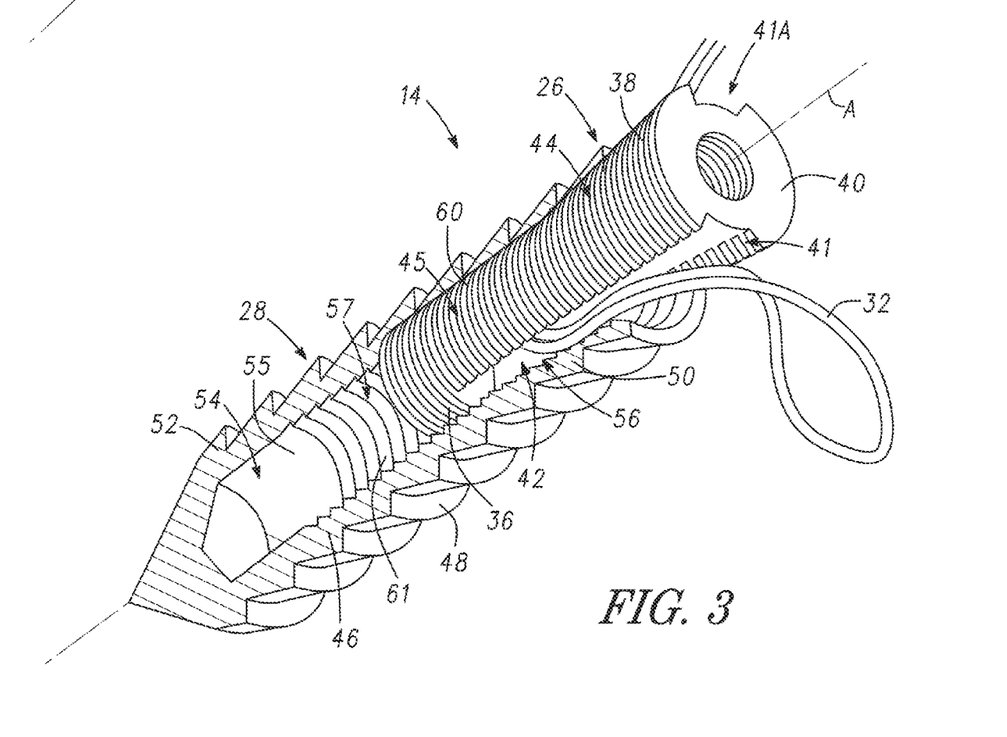
FIGS. 3 and 3A show a view of the anchoring device from FIG. 2 with an outer body shown in cross-section and the inner member shown in perspective in the non-deployed position in accordance with an example of the present application.
Figure 3A:
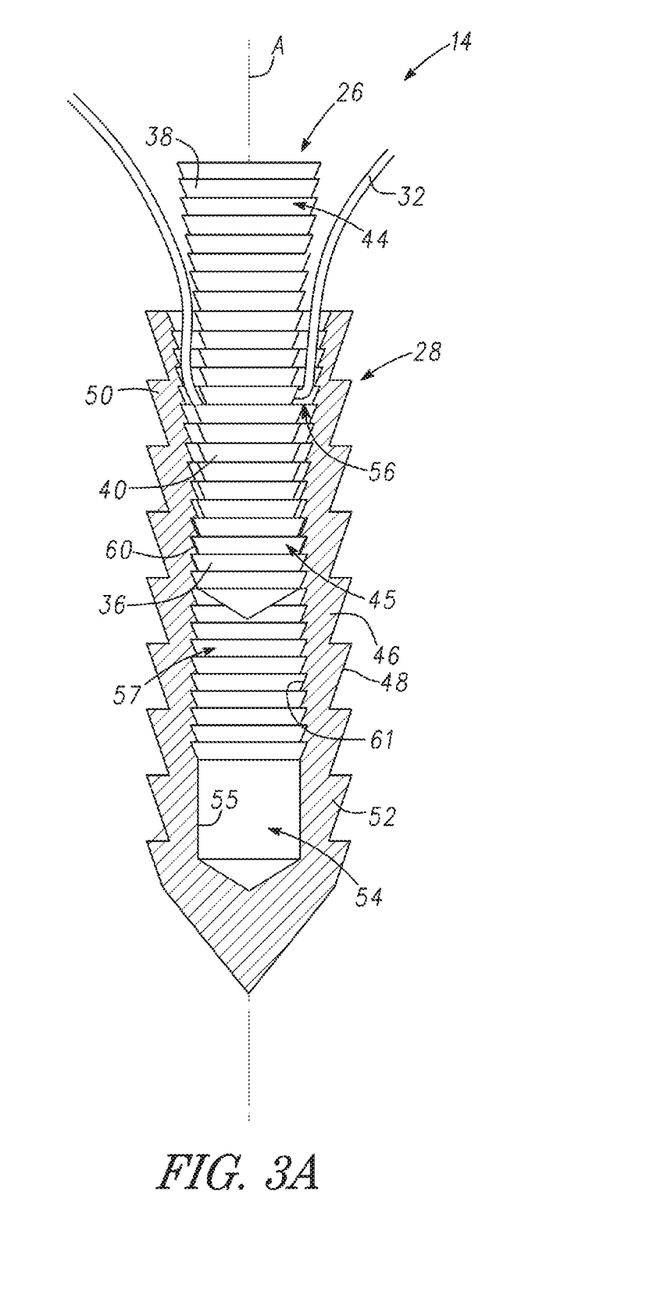

FIG. 2 shows a cross-section of the implantable anchor 14 coupled to the deployment member 22 of the deployment tool 12 with the inner member 26 in a first non-deployed position relative to the outer body 28 and the loop 32 received in an eyelet 42. In FIGS. 2, 3 and 3A, the outer cannula 20 (FIGS. 1 and 1A) has been removed and the inner shaft 23 is illustrated. As shown in FIG. 2, the implantable anchor 14 and indeed the inner shaft 23 and deployment member 22 can have an elongate shape extending along a longitudinal axis A. In the example of FIGS. 2, 3 and 3A, the implantable anchor 14 can be comprised of the inner member 26 and the outer body 28 each of which can have an elongate shape extending along the longitudinal axis A. The deployment member 22 can be configured to be detachable from the inner member 26 (e.g., by unscrewing or the like) and can be configured to be removable from the implantable anchor 14 according to some examples.

FIGS. 3 and 3A also show features of the implantable anchor 14 in addition to the inner member 26 and the outer body 28. For example, the inner member 26 can include a distal end portion 36, a proximal end portion 38, a body 40, a groove 41 (FIG. 3), a second groove 41A (FIG. 3), and the eyelet 42 (FIG. 3). The inner member 26 can include a tapered section 44 along an exterior of the proximal end portion 38. The outer body 28 can include a wall 46 having an outer surface 48 and an inner surface 55. The outer body 28 can additionally include a proximal end portion 50, a distal end portion 52, and an inner passage 54. The inner surface 55 can form the inner passage 54. The inner surface 55 can include a tapered section 56 along the proximal end portion 50.

As is shown in FIGS. 3 and 3A, the inner member 26 can be disposed in a first (non-deployed) position relative to the outer body 28. This allows for passage of the loop 32 in a proximally open cavity between the inner member 26 and the outer body 28. As will be discussed and illustrated subsequently, the inner member 26 and the outer body 28 can be configured to couple together in a manner that allows the inner member 26 to move proximally relative to outer body 28 into a second (deployed) position where the inner member 26 is received within the outer body 28 (example shown in FIGS. 7 and 8). More particularly, the inner shaft 23, deployment member 22 can be actuateable relative to the outer body 28 to move the inner member 26 to the second position relative to the outer body 28.

The distal end portion 36 of the inner member 26 can be configured having a somewhat uniform cross-sectional profile (i.e., the distal end portion 36 is un-tapered according to some examples). The distal end portion 36 can be configured to be received in an un-tapered portion of the inner passage 54 of the outer body 28 and can have mating features 60 (FIGS. 3 and 3A) configured to mate with corresponding mating features 61 (FIGS. 3 and 3A) along the inner surface 55 of the outer body 28. According to one example, the mating features 60, 61 can comprise one of threads or grooves.

According to one example, the inner member 26 can be configured as a compression plug that is configured to engage and be compressed against the inner surface 55 that defines the inner passage 54 of the outer body 28 when the inner member 26 is moved toward and into the second position. In some examples, only a first portion of a circumferential periphery of the inner member 26 is configured to engage and be compressed against the inner surface 55. In further examples, a second portion of the circumferential periphery of the inner member 26 comprises the groove 41 and a second groove 41A (FIGS. 3 and 5B) configured to receive the suture therein.

The inner member 26 can have a substantially circular cross-sectional shape (save for areas having groove 41 or the second groove 41A) as is further illustrated in the example of FIGS. 3, 3A, 5, 5A and 5B. The inner member 26 can be shaped and sized to be received in and substantially fill the inner passage 54 while still allowing for locking passage of the suture 16 through at least a portion of the inner passage 54 along the second groove 41A as will be illustrated and described subsequently.

The body 40 can extend along the longitudinal axis A and can have portions (sometimes referred to as quadrants or zones herein) of differing configuration as will be discussed subsequently in reference to FIGS. 5B and 6. The body 40 can extend longitudinally and can include the distal end portion 36 and the proximal end portion 38. The eyelet 42 (FIGS. 2 and 3) can extend through the body 40 and can generally be disposed between the distal end portion 36 and the proximal end portion 38.

Figure 7:
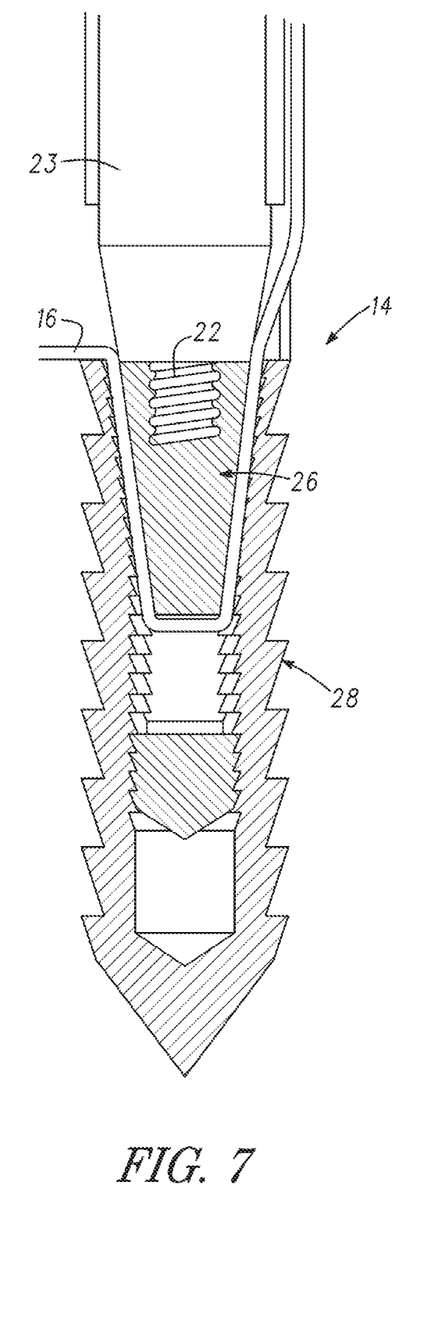
FIG. 7 shows the anchoring device of FIG. 3A but with the inner member moved to a second deployed position, the inner member and outer body receiving and passing suture through portions thereof in accordance with an example of the present application.
Figure 8:
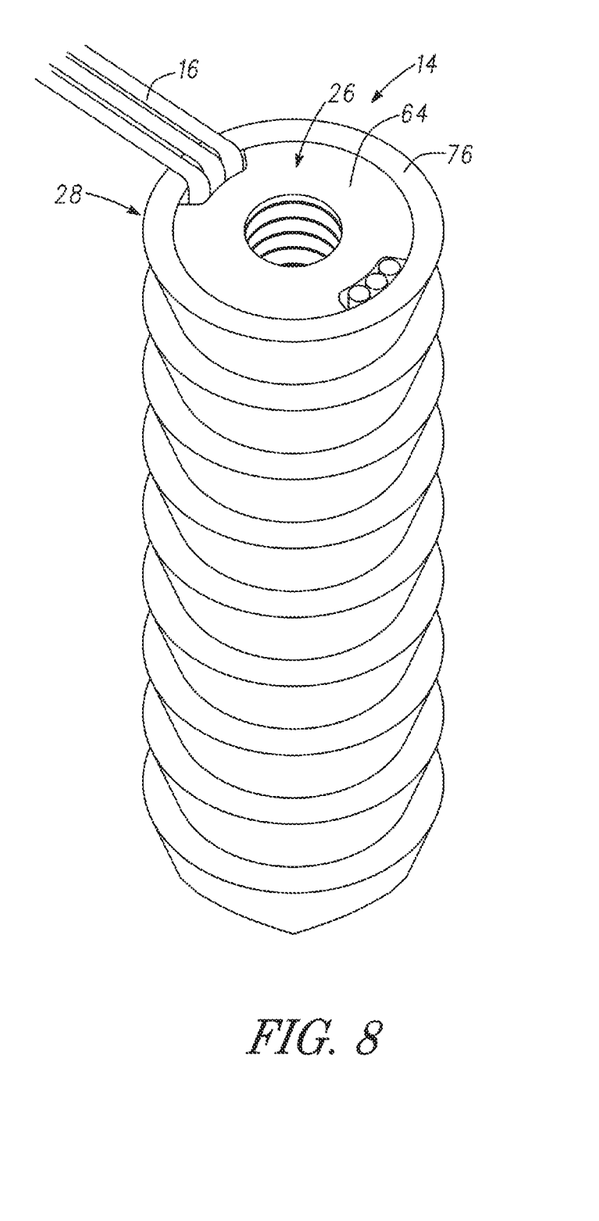
FIG. 8 shows a perspective view of the anchoring device with the inner member moved to the second deployed position and the deployment device decoupled from the anchoring device in accordance with an example of the present application.

According to some examples, the eyelet 42 can be sized to receive and allow for passage of either the loop 32 or the suture(s) 16 (FIGS. 7 and 8). The eyelet 42 can communicate with the groove 41 and the second groove 41A. This can allow for passage of the suture 16 or loop 32 from the groove 41 to the eyelet 42 and from the eyelet 42 to the second groove 41A.

As is best shown in FIG. 3, the groove 41 and the second groove 41A can extend generally longitudinally along at least a portion of a longitudinal length of the inner member 26. However, in other examples the groove 41 and/or the second groove 41A can be provided in the outer body 28 in addition to or in alternative to the inner member 26. Thus, the groove 41 and the second groove 41A can extend generally longitudinally along at least a portion of a longitudinal length of at least one of the outer body 28 and the inner member 26. The groove 41 and the second groove 41A can extend generally longitudinally (e.g., can be substantially aligned with longitudinal axis A). However, in some examples the groove 41 and/or the second groove 41A can vary at an angle from the longitudinal axis A by up to 20 degrees so as to traverse partially around a circumference of the outer body 28 and/or the inner member 26. The first groove 41 can be disposed on an opposing circumferential side of the inner member 26 from the second groove 41A.

The first groove 41 and the second groove 41A can be configured to receive the suture 16 (FIGS. 7 and 8) therein. More particularly, the groove 41 and the second groove 41A can be configured to have a width along a portion of the circumference of the outer body 28 and/or the inner member 26 that is appropriate to receive the loop 32 and/or the suture 16 (FIGS. 7 and 8) therein. Similarly, the depth of the groove 41 and the second groove 41A (as measured in a direction orthogonal to the longitudinal axis A) can be appropriately sized to receive the loop 32 and/or the suture 16 (FIGS. 7 and 8) therein. Further discussion of the configuration of the groove 41 and the second groove 41A will be discussed in reference to FIGS. 5B and 6.

As shown in FIG. 3A, in the first non-deployed position with the inner member 26 partially inserted into the inner passage 54 of the outer body 28 there can be a clearance (i.e. a proximally open cavity) between the tapered section 44 of the inner member 26 and the tapered section 56 of the outer body 28 such that the suture 16 and loop 32 need not be disposed in the groove 41 and the second groove 41A. The clearance can allow the loop 32 and/or suture 16 to pass into the outer body 28 and through the inner member 26 via the eyelet 42 in a somewhat unrestricted manner when the inner member 26 is in the first position as shown in FIG. 3A.

Turning to the outer body 28, the outer body 28 can comprise a shell with the inner passage 54 therein and with the wall 46 arranged around the inner passage 54. The wall 46 can extend from the inner surface 55 to the outer surface 48. The outer surface 48 can have features that facilitate coupling of the implantable anchor 14 in bone. For example, the outer surface 48 can be textured or otherwise configured with grooves, recesses or the like to facilitate engaging the bone. However, the outer surface 48 need not have surface features to engage the bone in all examples. For instance, the wall 46 can be smooth and/or compressible in some instances. The compression of the wall 46 and outer surface 48 can facilitate engagement with the bone.

The wall 46 can extend along the longitudinal axis A from the proximal end portion 50 to the distal end portion 52 and the inner surface 55 can define the inner passage 54. In the example of FIGS. 2, 3 and 3A, the inner surface 55 can have the tapered section 56 along the proximal end portion 50 and the proximal end portion 38 of the exterior surface the inner member 26 can have the tapered section 44. The tapered section 44 of the inner member 26 can be configured to engage with the tapered section 56 of the outer body 28 and can thereby create an interference fit where the inner member 26 is compressed against the outer body 28 when the inner member 26 is in the second position shown in FIGS. 7 and 8.

As is further shown in the example of FIGS. 3 and 3A, the inner surface 55 of the outer body 28 can have a non-tapered section 57 distal of the tapered section 56 and the exterior surface of the inner member 26 can have a non-tapered section 45 distal of the tapered section 44. According to further examples, the non-tapered section 45 of the inner member 26 is configured to engage with the non-tapered section 57 of the outer body 28 and can thereby create an interference fit where the inner member 26 is compressed against the outer body 28 when the member is in the second position shown in FIGS. 7 and 8.

Figure 4:
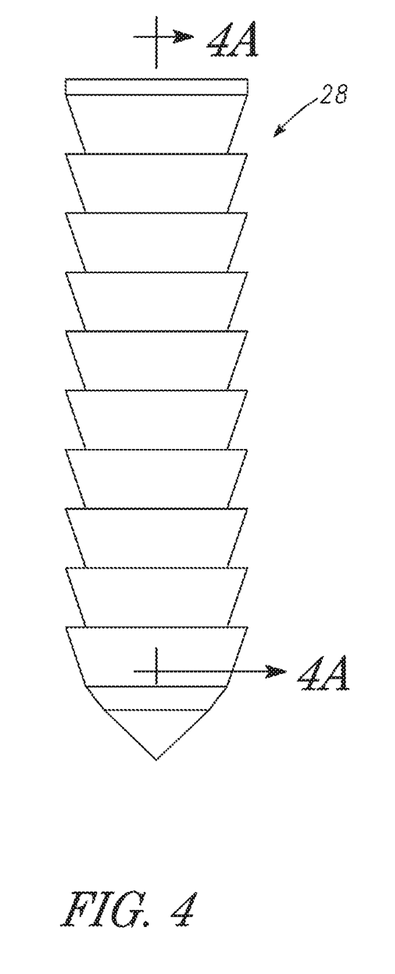
FIGS. 4 and 4A are views of the outer body of the anchoring device in accordance with an example of the present application.
Figure 4A:
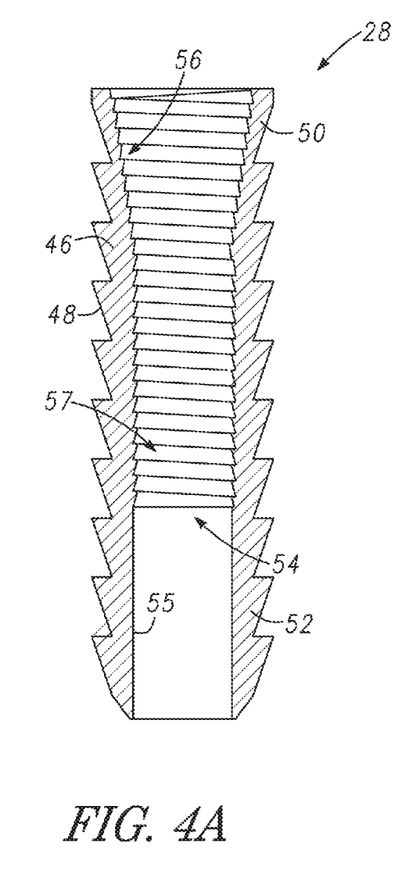

FIGS. 4 and 4A show the outer body 28 in further detail with the features discussed previously. In particular, FIG. 4A shows the wall 46 with the outer surface 48 and the inner surface 55, the proximal end portion 50, the distal end portion 52, and the inner passage 54. The inner surface 55 can include the tapered section 56 at the proximal end portion 50 and the non-tapered section 57 at the distal end portion 52.

In one example, the outer surface 48 can be provided with nine grooves and ridges along the outer surface thereof. The outer body 28 can have a depth of between 15 and 20 mm and can have a diameter of between 5 and 6 mm. As shown in FIG. 4A, the inner surface 55 can be configured with one of grooves and/or threads along at least a portion of the longitudinal length thereof. For example, the inner surface 55 can be configured with threads having a pitch of 0.5 mm and a tooth angle of 68 degrees and a depth of 0.13 mm. The tapered section 56 can be tapered at between 5 degrees and 10 degrees with respect to the longitudinal axis A. The inner passage 54 can have a diameter of 2.8 mm along the non-tapered section 57 of the inner surface 55.

Figure 5:
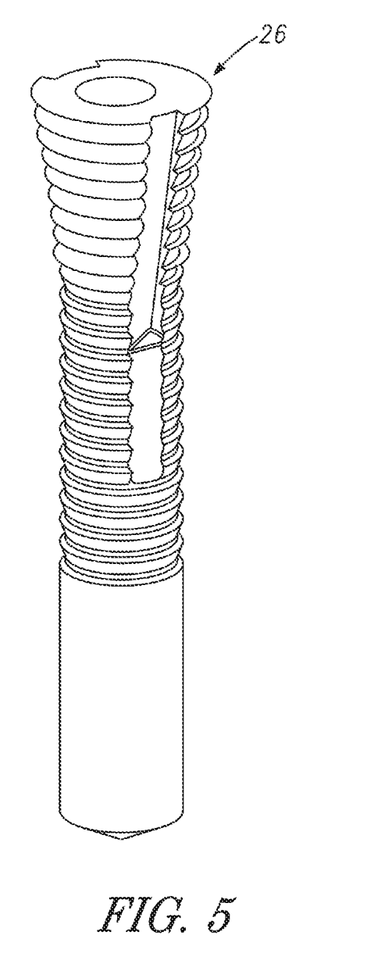
FIGS. 5, 5A and 5B are views of the inner member of the anchoring device in accordance with an example of the present application.
Figure 5A:
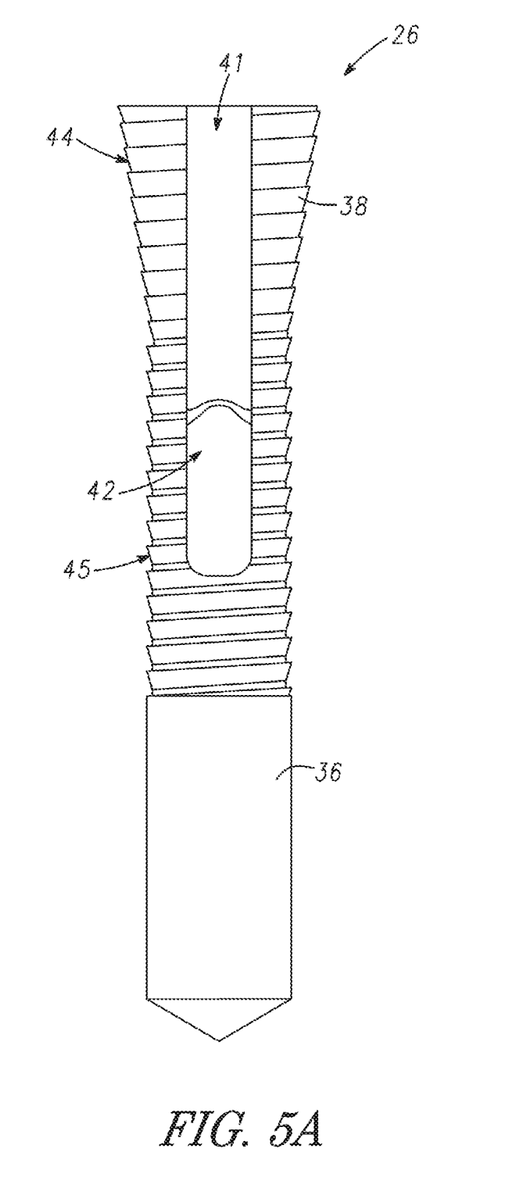
Figure 5B:
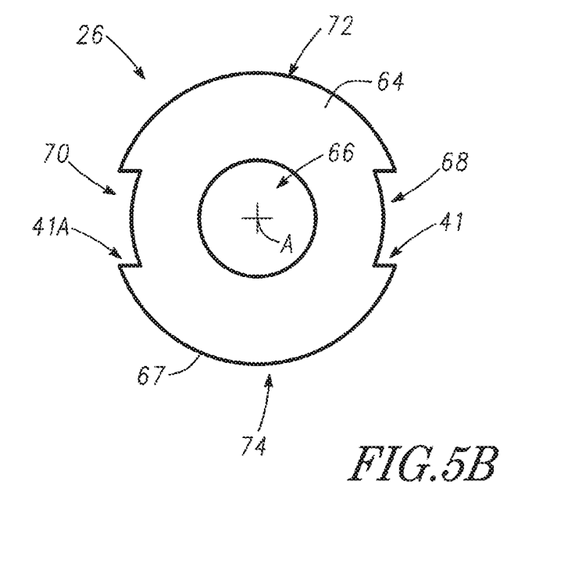
Figure 6:
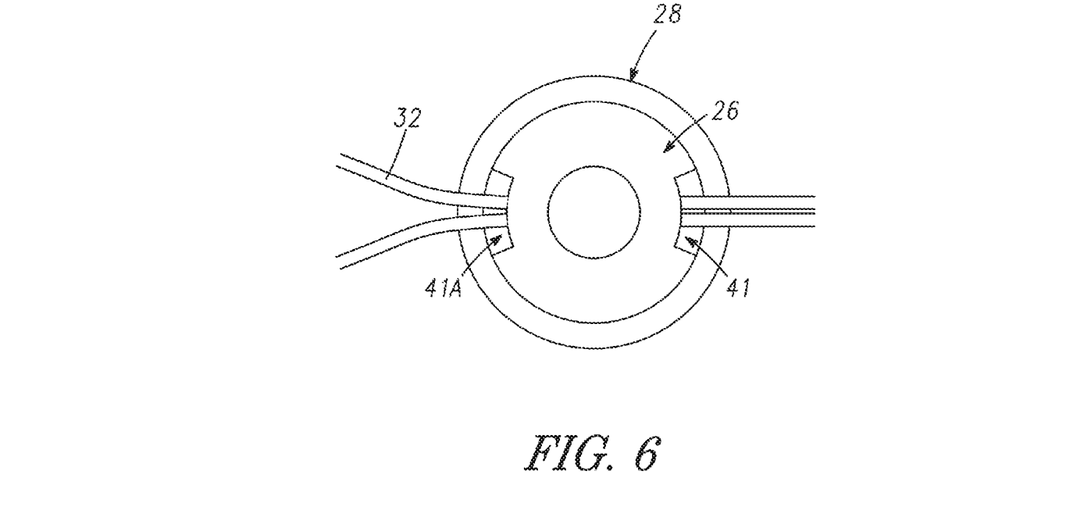
FIG. 6 is a plan view of a proximal portion of the inner member and the outer body showing grooves in the inner body that can facilitate passage of suture or the loop therealong in accordance with an example of the present application.

FIGS. 5, 5A and 5B show the inner member 26 in further detail with the features discussed. In particular, FIG. 5A shows the distal end portion 36, the proximal end portion 38, the body 40, the groove 41, and the eyelet 42. The body 40 can include the tapered section 44 at the proximal end portion 38 and the non-tapered section 45 at the distal end portion 36. According to the example of FIGS. 5 and 5A, a part of the distal end portion 36 may not include features such as thread and/or grooves but rather can be substantially smooth.

According to one example, the groove 41 can have a width in the circumferential direction of about 1.4 mm and a longitudinal extent of about 5.5 mm. The eyelet 42 can have a width of about 1.4 mm and a longitudinal length of about 4 mm. The inner body 26 can have a radius of curvature between the eyelet 42 and the groove 41 to facilitate ease of passage of the suture 16 therebetween. The radius can eliminate sharp corners that can potentially abrade or cut the suture 16. The distal end portion 36 can have features such as one of grooves or threads therealong. According to one example, the distal end portion 36 can have threads with a pitch that matches that of the inner surface 55 of the outer body 28. The distal end portion 36 can have an outer diameter of 3 mm and in inner diameter of 2.74 mm according to one embodiment. Thus, the distal end portion 36 at the non-tapered section 45 is configured to create an interference fit with the inner surface 55 (diameter of 2.8 mm) at the non-tapered section 57 when the inner member 26 is in the second position. Similarly, the tapered section 45 can be configured in a manner to create an interference fit with the tapered section 56.

FIG. 5B shows a proximal end 64 of the inner member 26 in plan view. FIG. 6 shows the inner member 26 of FIG. 5B partially received in the outer body 28 with the loop 32 passing through and received in the first groove 41 and the second grove 41A.

As shown in FIG. 5B, the inner member 26 can additionally include a coupling feature 66 that is configured to couple with the deployment member 22 (FIGS. 2 and 7). The coupling feature 66 can be either a female or male coupling feature, for example. In FIG. 5B, the coupling feature can be a bore having thread therealong configured to couple with corresponding thread and stud of the deployment member 22.

FIG. 5B also shows the exterior surface 67 of the inner member 26, when viewed in plan view or cross-section orthogonal to the longitudinal axis A, can have separate portions each having a different shape. These portion may be also be referred to a quadrants or zones herein. In particular, the example of FIG. 5B can have four portions comprising a first portion 68, a second portion 70, a third portion 72 and a fourth portion 74. In the example of FIG. 5B, the first portion 68 can comprise the groove 41. More particularly, the first portion 68 can comprise a part of the circumferential periphery of the exterior surface 67 along the groove 41. The second portion 70 can comprise the second groove 41A. More particularly, the second portion 70 can comprise a second part of the circumferential periphery of the exterior surface 67 along the second groove 41A. The third portion 72 can be disposed between first portion 68 and the second portion 70. Similarly, the fourth portion 74 can be disposed between first portion 68 and the second portion 70 on an opposing side of the inner member 26 from the third portion 72. The third portion 72 (and similarly the fourth portion 74) can comprise a section of the inner member 26 with mating features such as one of a groove and/or thread. Thus, the third portion 72 (and similarly the fourth portion 74) can comprise the periphery of the mating feature(s) along the exterior surface 67.

In some examples, the third portion 72 and the fourth portion 74 can be similarly configured having a same shape and size. At least one of the third portion 72 and the fourth portion 74 can be configured to engage corresponding mating features of the outer body 28 and can create an interference fit where the inner member 26 is compressed against the outer body 28 when the inner member 26 is in the second position with respect to the outer body 28. According to other examples the third portion 72 and the fourth portion 74 can be differently configured from one another. For example, the third portion 72 can have grooves while the fourth portion 74 may be smooth or non-circumferentially shaped without mating features.

In some examples, the first portion 68 and the second portion 70 can be differently configured. For example, the first portion 68 (comprising groove 41) can have a different depth in a direction orthogonal to the longitudinal axis than the second portion 70 (comprising the second groove 41A). In one example, the depth of the groove 41 can comprise 0.35 mm while the depth of the second groove 41A can comprise 0.25 mm. The different configuration of the groove 41 with respect to the groove 41A (and hence the first section 68 with respect to the second section 70) can be used to avoid applying an undesired additional amount of tension on the suture 16 passing along the groove 41 (i.e. the groove 41 is configured with a sufficient depth to allow the suture 16 to pass therealong without being captured and secured to be pull along with advancement of the inner member 26 relative to the outer body 28 as the inner member 26 is moved from the first position to the second position). In contrast, the second groove 41A can be configured such that the suture 16 passing therealong is capture and secured between the inner member 26 and the outer body 28. This capturing of the suture 16 can be due to compression of the inner member 26 by the outer body 28 in the vicinity of the second groove 41A and additionally or alternatively the depth of the second groove 41A, which can be relatively shallow enough relative to the diameter of the suture 16 in order to bring the suture 16 into contact with both the inner member 26 and the outer body 28 when the inner member 26 is advanced toward and into the second position. In other words, according to some examples, the first groove 41 (first portion 68) can be configured to avoid supplying extra tension to the suture 16 but can be configured to maintain a desired tension on the suture 16. The tapered section 44 can be configured to increase interference as the inner member 26 is inserted toward the second position. The third portion 72 and/or the fourth portion 74 can be configured to create an interference with the outer body 28. This interference can secure the inner member 26 within the outer body 28. The second groove 41A (second portion 70) can be configured to secure and retain the sutures 16 via compressive force between the inner member 26 and the outer body 28.

FIG. 7 shows the implantable anchor 14 with inner member 26 advanced by the deployment member 22 and the inner shaft 23 into the second deployed position where the inner member 26 is received in an interference fit with the outer body 28. FIG. 8 shows the implantable anchor 14 with the deployment tool including the deployment member 22 removed. As shown in FIG. 8, the suture 16 can be cut along one side of the implantable anchor 14 prior to, during or after the removal of the deployment device. In the example of FIGS. 7 and 8, in the second deployed position the proximal end 64 of the inner member 26 can be substantially flush with a proximal end 76 of the outer member 28. However, in other examples there can be a difference in termination height of the proximal end 64 relative to the proximal end 76.

Figure 9:
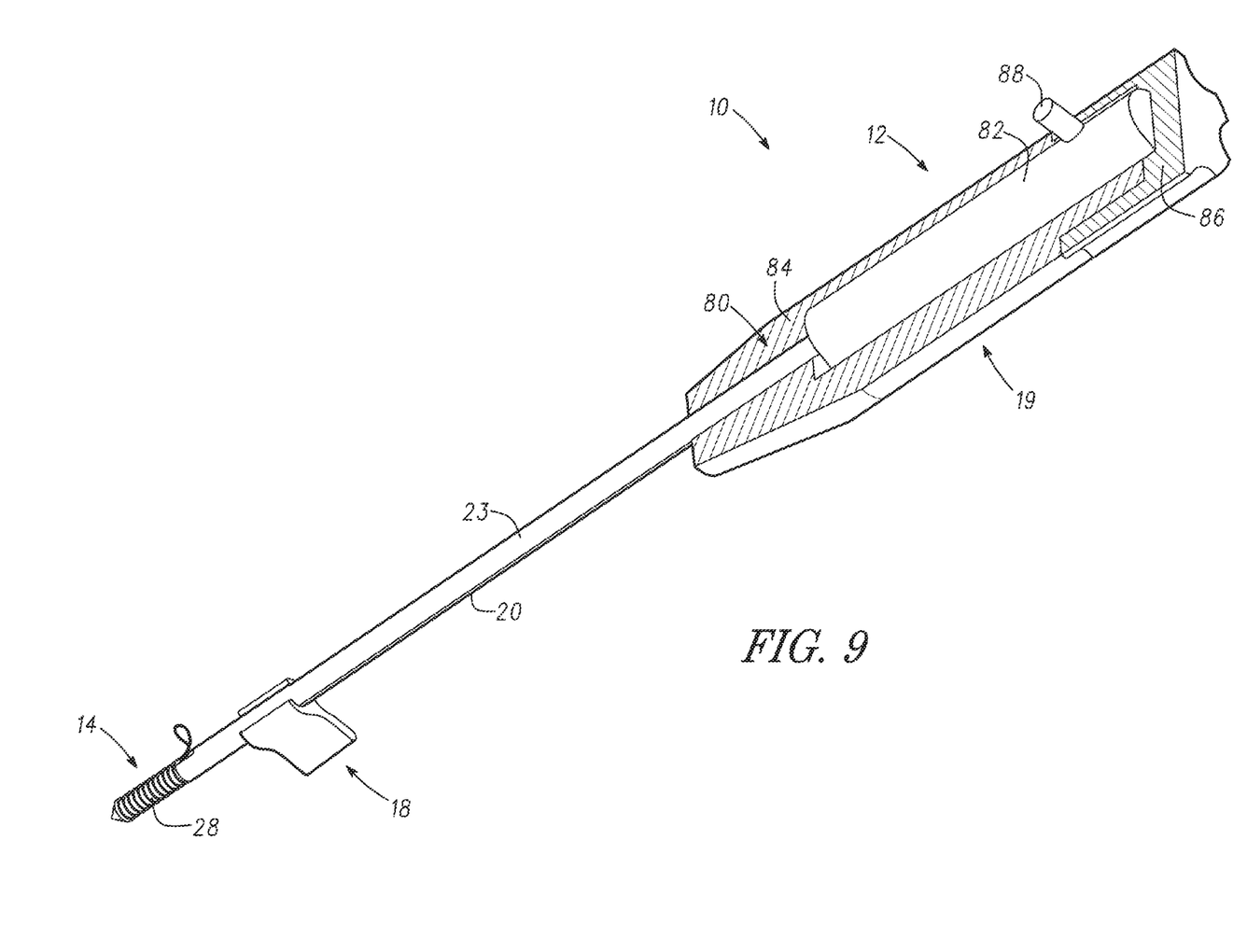
FIG. 9 shows the system of FIG. 1 with portions of the handle in cross-section to illustrate internal components including an actuation member and an inner shaft in accordance with an example of the present application.
Figure 10:
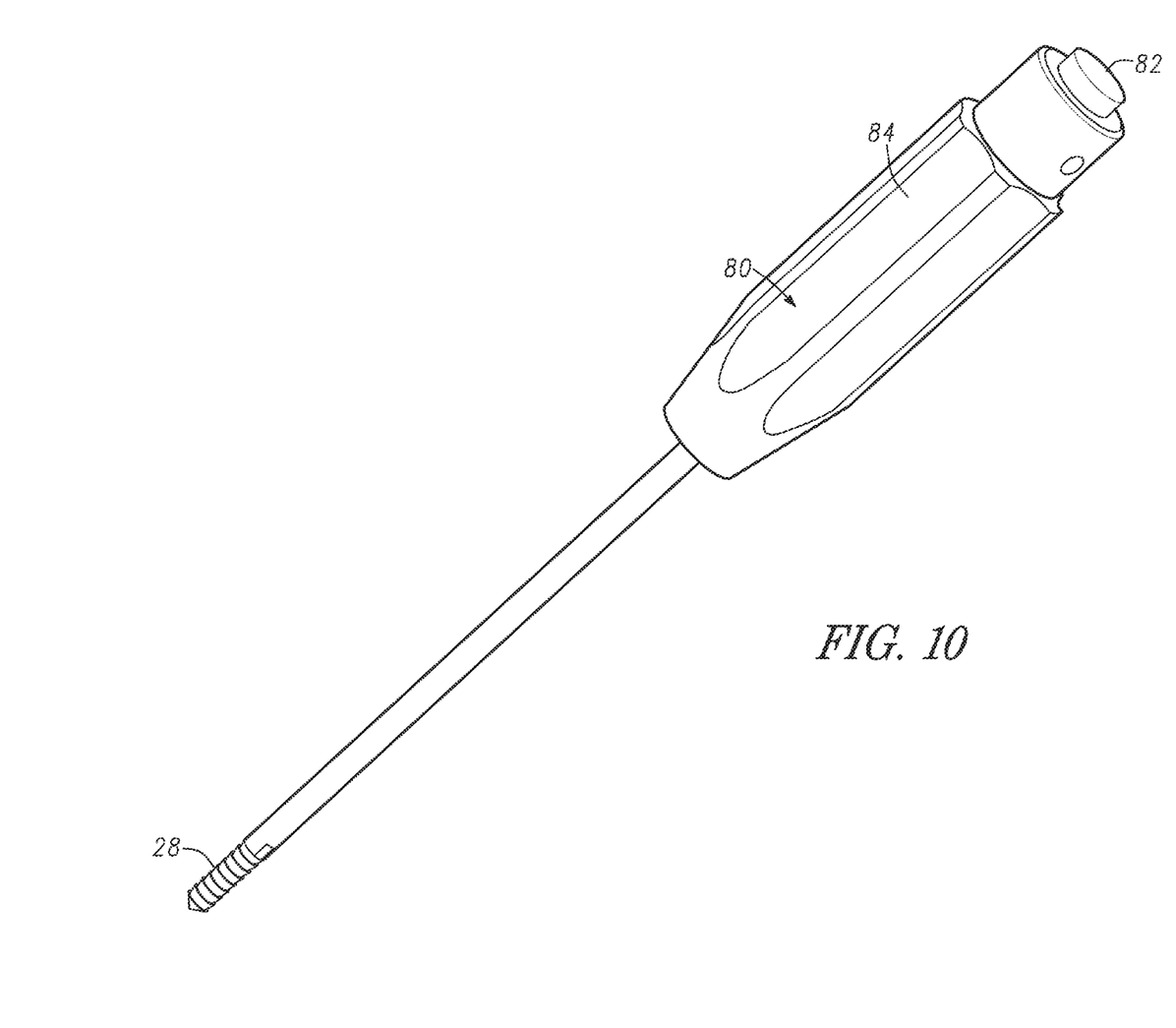
FIG. 10 shows the system of FIGS. 1 and 9 with a pin and a cap portion of the housing removed to allow a user to access the actuation member in accordance with an example of the present application.

FIG. 9 shows the system 10 including the deployment tool 12, the implantable anchor 14 and the threading device 18. In FIG. 9, portions of the outer cannula 20 and the proximal handle 19 comprising a housing 80 have been removed to show the inner shaft 23 and an actuation device 82. The housing 80 can have a main body portion 84 and a cap 86. A pin 88 (also shown in FIG. 1) can couple the cap 86 to the main body portion 84.

The inner shaft 23 can be coupled to the actuation device 82, which can be configured to be depressed by the user to facilitate a movement of the actuation device 82, the inner shaft 23 and the deployment member 22 (FIG. 7). As shown in FIG. 10, the actuation device 82 can be at least partially disposed within the housing 80 (e.g., in the main body portion 84) and a portion of the housing 80 (e.g., the cap 86 of FIG. 9) can be configured to be removable from a second portion of the housing 80 (e.g., the main body portion 84) thereby allowing the actuation device 82 to be depressed by the user.

More particularly, the cap 86 (FIG. 9) can remain coupled to the main body portion 84 via the pin 88 (FIG. 9) when the outer body 28 is initially inserted into and secured into the bone. The cap 86 (FIG. 9) can provide a surface that can be struck with a mallet or other tool to facilitate such insertion, for example. Upon insertion and securement of the implantable anchor 14 into the bone, the pin 88 can be removed, thereby allowing the cap 86 to be removed from the main body portion 84 as shown in FIG. 10. With removal of the cap 86 (FIG. 9) the actuation device 82 can be accessible to the user for actuation thereby. Actuation (e.g., pushing on the actuation device) can cause a linear translation of the actuation device 82, the inner shaft 23, the deployment member 22 (FIG. 7) and the inner member 26 (FIG. 7) relative to the outer body 28. In some cases, rather than simple linear translation items such as the actuation device 82, the inner shaft 23, the deployment member 22 and the inner member 26 can be rotated (e.g., if threading is used for connection between the inner member 26 and the outer body 28).

ADDITIONAL NOTES

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventor also contemplate examples in which only those elements shown or described are provided. Moreover, the present inventor also contemplate examples using any combination or permutation of those elements shown or described (or one or more aspects thereof), either with respect to a particular example (or one or more aspects thereof), or with respect to other examples (or one or more aspects thereof) shown or described herein.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) can be used in combination with each other. Other examples can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above detailed description, various features can be grouped together to streamline the disclosure. This should not be interpreted as intending that an unclaimed disclosed feature is essential to any claim. Rather, inventive subject matter can lie in less than all features of a particular disclosed example. Thus, the following claims are hereby incorporated into the detailed description as examples or embodiments, with each claim standing on its own as a separate example, and it is contemplated that such examples can be combined with each other in various combinations or permutations. The scope of the invention should be determined with reference to the appended claims, along with the full scope of equivalents to which such claims are entitled.

The claimed invention is:

1. A device for anchoring sutured tissue to a bone, the device comprising: an outer body comprising a shell with an outer surface thereof configured to engage the bone of a patient and an inner passage extending longitudinally along a longitudinal axis from a proximal end portion thereof toward a distal end portion, wherein an inner surface that defines the inner passage of the outer body has a tapered section along the proximal end portion; and an inner member configured to be disposed within the outer body and moveable longitudinally along the inner passage and the longitudinal axis relative to the outer body between a first position and a second position, wherein the inner member is configured with an eyelet to receive and pass a suture through the inner member, the inner member having an exterior surface comprising a periphery at a first portion with a first groove extending generally longitudinally along at least a portion thereof, the first groove configured to receive the suture therein, wherein the periphery at a second portion has a second groove extending generally longitudinally along at least a portion thereof, the second groove configured to receive the suture therein, wherein a depth of the first groove differs from a depth of the second groove in a direction orthogonal to the longitudinal axis along corresponding lengths of the first groove and the second groove with respect to the longitudinal axis, wherein the first groove and the second groove extend along an entire longitudinal length of a second tapered section to the eyelet, wherein, when the inner member is in the second position, the second tapered section of the inner member engages with the tapered section of the outer body and creates an interference fit whereby the inner member and the suture in the first groove is compressed against the outer such that the suture in the first groove is captured and secured but the suture in the second groove is moveable and is not captured or secured between the inner member and outer body.

2. The device of claim 1, wherein the inner surface of the outer body has a non-tapered section distal of the tapered section thereof and the exterior surface of the inner member has a non-tapered section distal of the second tapered section thereof, and wherein the non-tapered section of the inner member is configured to engage with the non-tapered section of the outer body and create an interference fit where the inner member is compressed against the outer body when the inner member is in the second position.

3. The device of claim 2, wherein the outer body has one or more features on the inner surface that defines the inner passage configured to mate with corresponding one or more features on the exterior surface of the inner member.

4. The device of claim 3, wherein the one or more features on the inner surface and the one or more features on the exterior surface comprise one or more of grooves and threads.

5. The device of claim 1, wherein the second groove is disposed on an opposing circumferential side of the exterior surface of the inner member from the first groove, and wherein the first groove and the second groove each extend from a proximal end of the inner member to communicate with the eyelet.

6. The device of claim 1, wherein the inner member has a coupling feature disposed at a proximal end portion thereof, the coupling feature configured to mate with an actuation member that advances the inner member from the first position to the second position.

7. The device of claim 1, wherein the first and second portions are spaced apart about a circumference of the inner member by third and fourth portions of the inner member, and wherein the third and fourth portions of the inner member are configured to engage and be compressed against an inner surface that defines the inner passage of the outer body when the inner member is in the second position.

8. A system for anchoring a sutured tissue to a bone, the system comprising: a suture; an outer body comprising a shell with an outer surface thereof configured to engage the bone of a patient and an inner passage extending longitudinally along a longitudinal axis from a proximal end portion thereof toward a distal end portion, wherein an inner surface that defines the inner passage of the outer body has a tapered section along the proximal end portion; an inner plug configured to be disposed within the outer body and moveable longitudinally along the inner passage and the longitudinal axis relative to the outer body between a first position and a second position, the inner plug having an eyelet configured to receive and pass the suture through the inner plug, wherein the inner plug has an exterior surface comprising a periphery at a first portion with a first groove extending generally longitudinally along at least a portion thereof, the first groove configured to receive the suture therein, wherein the periphery at a second portion has a second groove extending generally longitudinally along at least a portion thereof, the second groove configured to receive the suture therein, and wherein the first and second portions are spaced apart about a circumference of the inner plug by third and fourth portions of the inner plug; and a surgical tool comprising a deployment member, wherein the surgical tool is configured to actuate movement of the inner plug relative to the outer body between the first position and the second position via the deployment member that is coupleable to the inner plug, the deployment member configured to be detachable from the inner plug; wherein the second portion is configured differently from the first portion with the second groove having a different depth from the first groove in a direction orthogonal to the longitudinal axis along corresponding lengths of the first groove and the second groove with respect to the longitudinal axis, wherein a proximal end portion of the exterior surface defines a second tapered section, wherein the first groove and the second groove extend along an entire longitudinal length of the second tapered section to the eyelet, wherein the second tapered section of the inner plug including the third and fourth portions engages with the tapered section of the outer body and creates an interference fit, whereby, when the suture is received in the second groove and the inner plug is in the second position, the suture is captured and secured between the inner plug and outer body but when the suture is received in the first groove and the inner plug is in the second position, the suture is moveable and is not captured or secured between the inner plug and outer body.

9. The system of claim 8, wherein the surgical tool has an outer cannula, an inner shaft residing inside and movable relative to the outer cannula, and the deployment member is coupled to and extends from a distal end of the inner shaft, and wherein the inner shaft is coupled to an actuation device that is configured to be depressed by the user to facilitate a movement of the actuation device, the inner shaft and the deployment member.

10. The system of claim 9, wherein the actuation device is at least partially disposed within an outer housing comprising a handle, and wherein a portion of the outer housing is configured to be removable from a second portion of the outer housing thereby allowing the actuation device to be depressed by the user.

11. The system of claim 8, further comprising a threading tool, the threading tool having a loop configured to receive the one or more sutures and fit through the eyelet, and wherein the threading tool is configured to be mountable to the surgical tool.

12. A two-piece suture anchor for anchoring sutured tissue to a bone, the suture anchor comprising: an outer body comprising a shell with an outer surface thereof configured to engage the bone of a patient and an inner passage extending longitudinally along a longitudinal axis from a proximal end portion thereof toward a distal end portion, wherein an inner surface that defines the inner passage of the outer body has a tapered section along the proximal end portion; and an inner plug configured to be disposed within the outer body and moveable longitudinally along the inner passage and the longitudinal axis relative to the outer body between a first position and a second position, wherein the inner plug having an eyelet and an exterior surface comprising a periphery having a first portion with a first groove extending generally longitudinally along at least a portion thereof, the first groove configured to receive a suture therein, wherein the periphery has a second portion with a second groove extending generally longitudinally along at least a portion thereof, the second groove configured to receive the suture therein, and wherein a depth of the first groove differs from a depth of the second groove in a direction orthogonal to the longitudinal axis along corresponding lengths of the first groove and the second groove with respect to the longitudinal axis, wherein the eyelet comprises an orthogonal passage to the longitudinal axis extending through the inner plug and communicating with the first groove and the second groove, and wherein a proximal end portion of the exterior surface defines a second tapered section, wherein the first groove and the second groove extend along an entire longitudinal length of the second tapered section to the eyelet, wherein, when the inner plug is in the second position, the second tapered section of the inner plug engages with the tapered section of the outer body and creates an interference fit whereby the inner plug and the suture in the first groove is compressed against the outer body-such that the suture in the first groove is captured and secured but the suture in the second groove is moveable and is not captured or secured between the inner plug and outer body.

13. The two-piece suture anchor of claim 12, wherein the first and second portions are spaced apart about a circumference of the inner plug by third and fourth portions of the inner plug, and wherein the third and fourth portions of the inner plug are configured to engage and be compressed against an inner surface that defines the inner passage of the outer body when the inner plug is in the second position.

\* \* \* \* \*

UNITED STATES PATENT AND TRADEMARK OFFICE
CERTIFICATE OF CORRECTION

PATENT NO. : 10,729,420 B2
APPLICATION NO. : 15/133969
DATED : August 4, 2020
INVENTOR(S) : Cavallazzi et al.

Page 1 of 1

It is certified that error appears in the above-identified patent and that said Letters Patent is hereby corrected as shown below:

In the Claims

In Column 13, Line 3, in Claim 1, after "comprising:", insert --¶--

In Column 13, Line 9, in Claim 1, after "and", insert --¶--

In Column 13, Line 33, in Claim 1, after "and", insert --¶--

In Column 14, Line 6, in Claim 8, after "comprising:", insert --¶--

In Column 14, Line 6, in Claim 8, after "suture;", insert --¶--

In Column 14, Line 12, in Claim 8, after "portion;", insert --¶--

In Column 14, Line 27, in Claim 8, after "and", insert --¶--

In Column 14, Line 33, in Claim 8, after "plug;", insert --¶--

In Column 15, Line 5, in Claim 12, after "comprising:", insert --¶--

In Column 15, Line 12, in Claim 12, after "and", insert --¶--

In Column 16, Line 14, in Claim 12, delete "body-such" and insert --body such-- therefor Signed and Sealed this
Twenty-ninth Day of September, 2020

Andrei Iancu
*Director of the United States Patent and Trademark Office*